United States Patent [19]

Deraedt et al.

[11] 4,027,040
[45] May 31, 1977

[54] NOVEL BENZOPHENONE DERIVATIVES

[75] Inventors: Roger Deraedt, Pavillons-sous-Bois; Christian Marchandeau, Claye-Souilly; Jean Meier, La Varenne Saint-Hilaire, all of France

[73] Assignee: Roussel-UCLAF, Paris, France

[22] Filed: Nov. 7, 1975

[21] Appl. No.: 629,706

[30] Foreign Application Priority Data

Nov. 28, 1974 France .............................. 74.38981

[52] U.S. Cl. .............................. 424/331; 260/591; 260/517
[51] Int. Cl.² ................... A01N 9/24; C07C 49/80
[58] Field of Search ................... 260/591; 424/331

[56] References Cited

UNITED STATES PATENTS

| | | | |
|---|---|---|---|
| 2,671,016 | 3/1954 | Erickson et al. | 260/591 |
| 2,802,032 | 8/1957 | Prill | 260/591 |
| 3,898,275 | 8/1975 | Houlihan | 260/591 |
| 3,924,002 | 12/1975 | Duennenberger et al. | 260/591 |
| 3,931,302 | 1/1976 | Allais et al. | 260/591 |

FOREIGN PATENTS OR APPLICATIONS 2,241,560  8/1973  Germany .............................. 260/592

*Primary Examiner*—Bernard Helfin
*Assistant Examiner*—James H. Reamer
*Attorney, Agent, or Firm*—Hammond & Littell

[57] ABSTRACT

Novel benzophenone derivatives of the formula

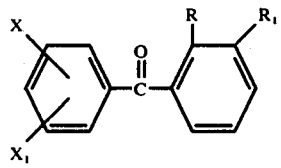

wherein X and $X_1$ are individually selected from the group consisting of hydrogen, halogen, alkyl of 1 to 5 carbon atoms, alkoxy of 1 to 5 carbon atoms, alkylthio of 1 to 5 carbon atoms, $CF_3O-$, $CF_3S-$ and $CF_3-$, R is selected from the group consisting of hydrogen and alkyl of 1 to 5 carbon atoms and $R_1$ is an aliphatic hydrocarbon of the formula

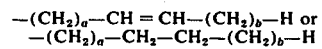

where $a$ and $b$ are whole numbers between 0 and 16 and whose sum is not greater than 16 which have a very clear analgesic activity.

17 Claims, No Drawings

NOVEL BENZOPHENONE DERIVATIVES

STATE OF THE ART

U.S. Pat. No. 3,741,988 and Belgium Pat. No. 824,658 both disclose benzophenones having analgesic and anti-inflammatory activity but the compounds in each patent possess a carboxyl group in a side chain.

OBJECTS OF THE INVENTION

It is an object of the invention to provide novel benzophenones of formula I and a novel method of preparing the said compounds.

It is a further object of the invention to provide novel analgesic compositions and to provide a novel method of relieving pain in warm-blooded animals.

These and other objects and advantages of the invention will become obvious from the following detailed description.

THE INVENTION

The novel benzophenones of the invention have the formula

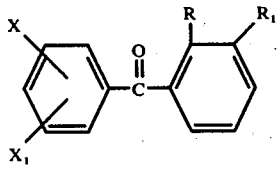
I wherein X and $X_1$ are individually selected from the group consisting of hydrogen, halogen, alkyl of 1 to 5 carbon atoms, alkoxy of 1 to 5 carbon atoms, alkylthio of 1 to 5 carbon atoms, $CF_3O$, $CF_3S-$ and $CF_3-$, R is selected from the group consisting of hydrogen and alkyl of 1 to 5 carbon atoms and $R_1$ is an aliphatic hydrocarbon of the formula

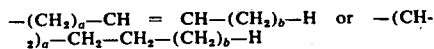

where $a$ and $b$ are whole numbers between 0 and 16 and whose sum is not greater than 16.

When X or $X_1$ are halogen, they are preferably chlorine or fluorine but they may also be bromine or iodine. When X and $X_1$ may also be alkyl, alkoxy or alkylthio, they preferably have 1 to 3 carbon atoms such as methyl, ethyl, n-propyl, methylthio, ethylthio, n-propylthio, methoxy, ethoxy or n-propoxy. When R is alkyl, it is preferably methyl, ethyl or n-propyl.

A preferred group of compounds of formula I are those where X is hydrogen, $X_1$ is halogen, R is alkyl of 1 to 5 carbon atoms, preferably methyl and $R_1$ is an aliphatic hydrocarbon of 2 to 7 carbon atoms.

The novel process of the invention for the preparation of compounds of formula I comprises condensing by the Wittig reaction a compound of the formula

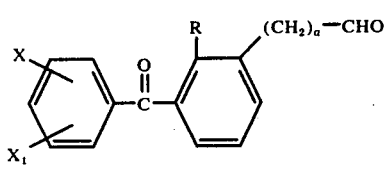
II with a compound of the formula $$(C_6H_5)_3-P=CH-(CH_2)_bH$$
III wherein X, $X_1$, R, $a$ and $b$ have the above definitions to obtain a compound of the formula

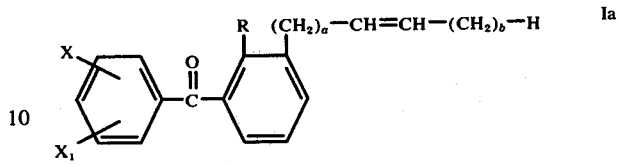
Ia which if desired may be reacted with a reducing agent to obtain a compound of the formula

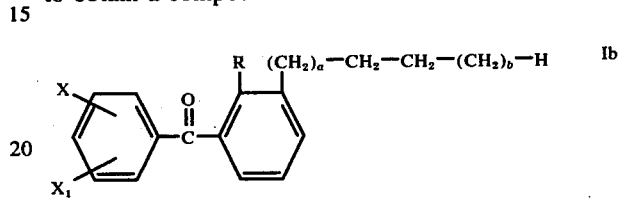
Ib

In a preferred mode of the process, the compound of formula III is prepared by reacting a strong base with a quaternary phosphonium halide of the formula

IVa wherein Hal is halogen, preferably bromine or iodine. The Wittig reaction is effected in a solvent such as benzene, toluene, tetrahydrofuran or dimethylsulfoxide, preferably in a mixture of anhydrous tetrahydrofuran and dimethylsulfoxide. The reduction is a hydrogenation in the presence of a catalyst such as Raney nickel or platinum oxide and is preferably effected in a solvent such as alkanols like methanol, ethanol or isopropanol.

The starting materials of formula II may be prepared by known procedures. When $a$ is 0, a compound of the formula

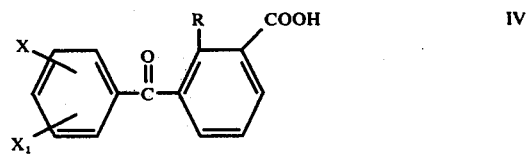
IV (prepared by the process described in French Pat. No. 2,085,638) is converted into the corresponding acid chloride which is then catalytically reduced in the presence of palladized barium sulfate by the method of Rosenmund to obtain the corresponding compound of the formula

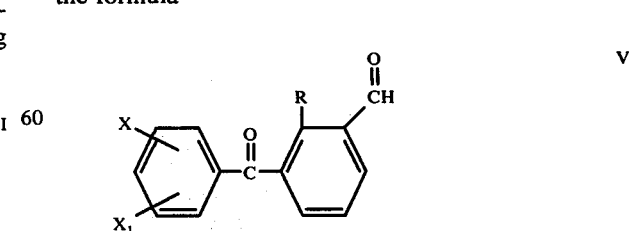
V

In the compounds of formula II where $a$ is 1, these may be prepared by reacting a compound of the formula

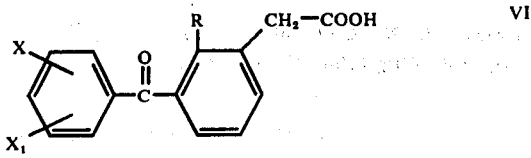

(prepared by the process described in French medical Pat. No. 8440M) in the same conditions as described above to obtain the desired compound of formula II. When a is 2 to 16, a compound of formula V is reacted with a compound of the formula

$(C_6H_5)_3-P=CH-(CH_2)_p-COOR_2$ wherein p is a number from 0 to 14 and $R_2$ is lower alkyl or an alkali metal, saponifying the latter to the free acid if $R_2$ is alkyl and converting the acid to its acid chloride and catalytically reducing the latter with palladized barium sulfate.

The compounds of formula IVa may be prepared by reacting triphenylphosphine with a compound of the formula Hal—$(CH_2)_b$—$CH_3$ in an anhydrous solvent such as ether, benzene, toluene or xylene or without a solvent.

The novel analgesic compositions of the invention are commprised of an effective amount of at least one compound of formula I and a carrier. The compositions may be in the form of tablets, sublingual tablets, dragees, capsules, gelules, drinkable solutions or emulsions, injectable solutions or suspensions, suppositories, creams, pomades or lotins prepared in the usual fashion.

The analgesic compositions are useful for the treatment of muscular, articular or nervous pains, dental pain and migraines.

The compositions may contain the usual excipients used in pharmaceuticals such as aqueous or non-aqueous vehicles, talc, gum arabic, lactose, starch, magnesium stearate, cacao butter, animal or vegetable fatty bodies, paraffinic derivatives, glycols, preservatives and diverse wetting agents, dispersants or emulsifiers.

The novel method of the invention for relieving pain in warm-blooded animals comprises administering to warm-blooded animals an analgesically effective amount of at least one compound of formula I. The active compounds may be administered orally, rectally, locally, perlingually or parenterally. The usual daily effective dose is 1 to 40 mg/kg depending on the product and the method of administration.

In the following examples there are described several preferred embodiments to illustrate the invention. However, it should be understood that the invention is not intended to be limited to the specific embodiments.

EXAMPLE 1

4-chloro-3′-(1″-n-heptenyl)-2′-methyl-benzophenone

STEP A: 2-methyl-3-(p-chlorobenzoyl)-benzaldehyde

A mixture of 43.92 g of 2-methyl-3-(p-chlorobenzoyl)-benzoic acid chloride, 450 ml of xylene, 4.5 g of barium sulfate containing 10% palladium and 0.4 ml of a solution obtaining by refluxing 6 g of quinolein and 1 g of sulfur for 5 hours was cooled and then was diluted with 70 ml of xylene. The mixture was stirred at 130° C while passing hydrogen therethrough for 45 minutes and the said temperature was held until evolution of hydrochloric acid ceased. An inert gas was passed therethrough at 130° C and the mixture was then cooled to 30° C and filtered to remove the catalyst. The solvent was distilled off and the residual oil was dissolved in isopropyl ether. Sodium bisulfite was added to the resulting solution and the mixture was stirred for 18 hours. The bisulfitic compound which precipitated was recovered by vacuum filtration, was washed and was then decomposed by stirring for 2½ hours in the presence of dilute sulfuric acid and ether under an inert gas. The ether was decanted and the aqueous phase was extracted with ether. The combined ether phases were washed with water, dried and evaporated to dryness under reduced pressure. The residue was crystallized from isopropyl ether to obtain 24.3 g of 2-methyl-3-(p-chlorobenzoyl)-benzaldehyde melting at 68° C.

STEP B: n-hexyl-triphenylphosphonium iodide

A mixture of 28.82 g of triphenylphosphine, 21.2 g of 1-iodo-hexane and 200 ml of xylene was refluxed for 5 hours and then was cooled. The solvent was decanted and the gummy residue was triturated with ether and dried at 90° to 100° C under reduced pressure to obtain 44.53 g of n-hexyltriphenylphosphonium iodide melting at 106° C.

STEP C: 4-chloro-3′-(1″-n-heptenyl)-2′-methyl-benzophenone

A solution of 9.955 g of n-hexyl triphenylphosphonium iodide, 5.17 g of a 2-methyl-3-(p-chlorobenzoyl)-benzaldehyde and 100 ml of a 1—1 dimethylsulfoxide-tetrahydrofuran mixture at 0° C was added with stirring to a suspension of 880 mg of 60% sodium hydride in mineral oil previously washed with petroleum ether in 20 ml of a 1—1 dimethylsulfoxide-tetrahydrofuran mixture and the mixture was stirred for 10 minutes at 0° C and then for 4½ hours at room temperature. The solvents were evporated under reduced pressure and the residue in ethyl ether was heated to reflux. The mixture was decanted and the procedure was repeated 3 times under the same conditions. The ether extracts were evaporated to dryness and the 12.4 g of oily residue was chromatographed over silica gel in benzene to obtain 5.645 g of 4-chloro-3′-(1″-n-heptenyl)-2′-methyl-benzophenone in the form of an oil.

Analysis: $C_{21}H_{23}ClO$: Calculated: %C 77.16; %H 7.09; %Cl 10.85; Found: %C 78.2; %H 7.5; %Cl 10.7

EXAMPLE 2

4-chloro-3′-n-heptyl-2′-methyl-benzophenone 5.57 g of 4-chloro-3′-(1″-heptenyl)-2′-methyl-benzophenone were added to a suspension of 60 ml of ethanol and 110 mg of platinum oxide and the mixture was stirred under a hydrogen atmosphere for 20 minutes. The mixture was then filtered and the filtrate was evaporated to dryness. The residue in benzene was chromatographed over silica gel to obtain 4.87 g of 4-chloro-3′-(n-heptyl)-2′-methyl-benzophenone in the form of an oil.

Analysis: $C_{21}H_{25}ClO$: Calculated: %C 76.69; %H 7.66; %Cl 10.78; Found: %C 76.5; %H 7.7; %Cl 10.8

EXAMPLE 3

4-chloro-3′-(1″-hexenyl)-2′-methyl-benzophenone

STEP A: n-pentyl-triphenylphosphonium iodide

Using the procedure of Step B of Example 1, n-pentyl iodide and triphenylphosphine were reacted to obtain n-pentyl-triphenylphosphonium iodide melting at 174° C.

STEP B:
4-chloro-3'-(1''-hexenyl)-2'-methyl-benzophenone

Using the procedure of Example 1, 9.66 g of n-pentyl triphenylphosphonium iodide and 5.17 g of 2-methyl-3-(p-chlorobenzoyl)-benzaldehyde were reacted to obtain 5.785 g of 4-chloro-3'-(1''-hexenyl)-2'-methyl-benzophenone in the form of an oil.

Analysis: $C_{20}H_{21}ClO$: Calculated: %C 76.78; %H 6.77; %Cl 11.33; Found: %C 77.1; %H 6.9; %Cl 11.2

EXAMPLE 4

4-chloro-3'-(n-hexyl)-2'-methyl-benzophenone

Using the procedure of Example 2, 5.7 g of 4-chloro-3'-(1''-hexenyl)-2'-methyl-benzophenone were reacted to obtain 3.73 g of 4-chloro-3'-(n-hexyl)-2'-methyl-benzophenone in the form of an oil.

Analysis: $C_{20}H_{23}ClO$: Calculated; %C 76.29; %H 7.36; %Cl 11.26; Found: %C 76.2; %H 7.4; %Cl 11.3

EXAMPLE 5

4-chloro-3'-(3''-butenyl)-2'-methyl-benzophenone

Using the procedure of Example 1, triphenyl methyl phosphonium bromide and 3-(p-chlorobenzoyl)-2-methyl-phenylpropionaldehyde were reacted to obtain 4-chloro-3'-(3''-butenyl)-2'-methyl-benzophenone.

Analysis: $C_{18}H_{17}ClO$: Calculated: %C 75.91; %H 6.02; %Cl 12.45; Found: %C 76.0; %H 6.2; %Cl 12.5

EXAMPLE 6

4-chloro-3'-(n-butyl)-2'-methyl-benzophenone

Using the procedure of Example 2, 9.01 g of 4-chloro-3'-(3''-butenyl)-2'-methyl-benzophenone were reacted to obtain 7.09 g of 4-chloro-3'-(n-butyl)-2'-methyl-benzophenone.

Analysis: $C_{18}H_{19}ClO$: Calculated: %C 75.38; %H 6.68; %Cl 12.36; Found: %C 75.5; %H 6.9; %Cl 12.4

EXAMPLE 7

4-chloro-3'-(2''-butenyl)-2'-methyl-benzophenone

STEP A: 2-methyl-3-(p-chlorobenzoyl)-phenylacetic acid

A mixture of 5 g of 2-methyl-3-(p-chlorobenzoyl)-benzoic acid and 50 ml of thionyl chloride was heated for 2 hours and excess thionyl chloride was then distilled under reduced pressure. The acid chloride formed was dissolved in methylene chloride and the solution was added progressively to 370 ml of a solution of diazomethane in methylene chloride cooled to 0° C. The mixture stood overnight at room temperature and the solvent was distilled under reduced pressure. The resulting diazoketone was dissolved in 30 ml of dioxane and the solution was progressively added at 70° C to a mixture of 6 g of silver oxide, 14.5 g of sodium carbonate, 9.6 g of sodium thiosulfate and 70 ml of water. After being held at 70° C for 2 hours, the mixture was filtered and the filtrate was acidified with concentrated hydrochloric acid. The precipitate formed was recovered and was washed with water and crystallized from isopropyl ether to obtain 2-methyl-3-(p-chlorobenzoyl)-phenylacetic acid melting at 152° C.

STEP B: 2-methyl-3-(p-chlorobenzoyl)-phenylacetic acid chloride

A solution of 5.8 g of 2-methyl-3-(p-chlorobenzoyl)-phenylacetic acid in 25 ml of thionyl chloride was refluxed for 1½ hours and excess thionyl chloride was removed to obtain 2-methyl-3-(p-chlorobenzoyl)-phenylacetic acid chloride melting at 62°–63° C.

STEP C:
2-methyl-3-(p-chlorobenzoyl)-phenylacetaldehyde

Using the procedure of Step A of Example 1, 2-methyl-3-(p-chlorobenzoyl)-phenylacetic acid chloride was reduced to form 2-methyl-3-(p-chlorobenzoyl)-phenylacetaldehyde in the form of an oil.

Analysis: $C_{16}H_{13}ClO_2$: Calculated: %C 70.46; %H 4.8; %Cl 13.0; Found: %C 70.5; %H 4.6; %Cl 13.6

STEP D:
4-chloro-3'-(2''-butenyl)-2'-methyl-benzophenone

Using the procedure of Step B of Example 1, 8.065 g of 2-methyl-3-(p-chlorobenzoyl)-phenylacetaldehyde and 11 g of triphenyl ethyl phosphonium bromide were reacted to obtain 2.54 g of 4-chloro-3'-(2''-butenyl)-2-methyl-benzophenone in the form of an oil.

Analysis: $C_{18}H_{17}ClO$: Calculated: %C 75.91; %H 6.02; %Cl 12.45; Found: %C 76.2; %H 6.1; Cl 12.4

EXAMPLE 8

4-fluoro 3'-(n-butyl) 2'-methyl benzophenone

Using the procedure of Examples 1 and 2, 2-methyl-3-(p-fluorobenzoyl)-benzaldehyde and n-propyl-triphenyl phosphonium iodide were reacted to obtain 4-fluoro-3'-(butenyl)-2'-methyl-benzophenone which was hydrogenated to form 4-fluoro-3'-(n-butyl)-2'-methyl-benzophenone in the form of an oil.

Analysis: $C_{18}H_{21}FO$: Calculated: %C 79.97; %H 7.08; %F 7.03; Found: %C 80.3; %H 7.1; %F 7.0

EXAMPLE 9

A gelule was prepared from 50 mg of the product of Example 7 and sufficient polyoxyethylene glycol to prepare a gelule.

PHARMACOLOGICAL STUDY OF ANALGESIC ACTIVITY

The test is based on that of Koster et al. [Fed. Proc., Vol. 18 (1959), p. 412] in which an intraperitoneal injection of acetic acid provokes in mice repeated stretching and twisting movements for at least 6 hours and an analgesic prevents or diminishes this syndrome which is considered to be an exterioralization of a diffuse abdominal pain. A 1% solution of acetic acid in water containing 10% of gum arabic was used and the dose for inducing this syndrome under these conditions was 0.01 ml/g or 100 mg/kg of acetic acid. The test products were orally administered one-half hour before the acetic acid injection and the mice were fasted for 24 hours before the test. The stretchings were observed for 15 minutes each mouse and totaled commencing right after the acetic acid injection. The results were expressed as $DA_{50}$, the dose permitting a 50% diminution in the number of stretchings compared to the controls. The results are reported in Table I.

TABLE I

| Examples | $DA_{50}$ mg/kg |
| --- | --- |
| 3 | 20 |
| 7 | 7 |
| 4 | 9 |
| 5 | 22 |
| 6 | 8 |
| 2 | 30 |
| 8 | 15 |

Various modifications of the products and processes of the invention may be made without departing from the spirit or scope thereof and it should be understood that the invention is to be limited only as defined in the appended claims.

We claim:

1. A benzophenone of the formula

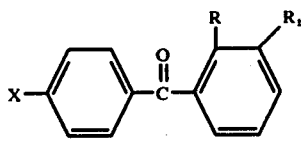

wherein R is alkyl of 1 to 5 carbon atoms, X is halogen and $R_1$ is an aliphatic hydrocarbon of the formula

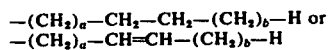

wherein $a$ and $b$ are whole numbers between 0 and 5 and their sum is not greater than 5.

2. A compound of claim 1 where R is methyl.

3. A compound of claim 1 which is 4-chloro-3'-(1''-n-heptenyl)-2'-methyl-benzophenone.

4. A compound of claim 1 which is 4-chloro-3'-(n-heptyl)-2'-methyl-benzophenone.

5. A compound of claim 1 which is 4-chloro-3'-(1''-hexenyl)-2'-methyl-benzophenone.

6. A compound of claim 1 which is 4-chloro-3'-(n-hexyl)-2'-methyl-benzophenone.

7. A compound of claim 1 which is 4-chloro-3'-(3''-butenyl)-2'-methyl-benzophenone.

8. A compound of claim 1 which is 4-chloro-3'-(2''-butenyl)-2'-methyl-benzophenone.

9. A compound of claim 1 which is 4-chloro-3'-(n-butyl)-2'-methyl-benzophenone.

10. A compound of claim 1 which is 4-fluoro-3'-(1''-butenyl)-2'-methyl-benzophenone.

11. A compound of claim 1 which is 4-fluoro-3'-(n-butyl)-2'-methyl-benzophenone.

12. An analgesic composition comprising an effective amount of at least one compound of claim 1 and a pharmaceutical carrier.

13. A method of relieving pain in warm-blooded animals comprising administering to warm-blooded animals an analgesically effective amount of at least one compound of claim 1.

14. The method of claim 13 wherein the compound is 4-chloro-3'-(1''-hexenyl)-2'-methyl-benzophenone.

15. The method of claim 13 wherein the compound is 4-chloro-3'-(3''-butenyl)-2'-methyl-benzophenone.

16. The method of claim 13 wherein the compound is 4-chloro-3'-(2''-butenyl)-2'-methyl-benzophenone.

17. The method of claim 13 wherein the compound is 4-chloro-3'-(n-butyl)-2'-methyl-benzophenone.

* * * * *